US011572589B2

(12) United States Patent
Murphy et al.

(10) Patent No.: US 11,572,589 B2
(45) Date of Patent: Feb. 7, 2023

(54) METHOD FOR PREDICTION OF ACUTE REJECTION AND RENAL ALLOGRAFT LOSS USING PRE-TRANSPLANT TRANSCRIPTOMIC SIGNATURES IN RECIPIENT BLOOD

(71) Applicant: Icahn School of Medicine at Mount Sinai, New York, NY (US)

(72) Inventors: Barbara Murphy, Pelham Manor, NY (US); Weijia Zhang, Cresskill, NJ (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 79 days.

(21) Appl. No.: 17/046,692

(22) PCT Filed: Apr. 16, 2019

(86) PCT No.: PCT/US2019/027618
§ 371 (c)(1),
(2) Date: Oct. 9, 2020

(87) PCT Pub. No.: WO2019/204267
PCT Pub. Date: Oct. 24, 2019

(65) Prior Publication Data
US 2022/0090197 A1    Mar. 24, 2022

Related U.S. Application Data

(60) Provisional application No. 62/658,066, filed on Apr. 16, 2018.

(51) Int. Cl.
*C12Q 1/6883* (2018.01)
(52) U.S. Cl.
CPC ..... *C12Q 1/6883* (2013.01); *C12Q 2600/158* (2013.01)
(58) Field of Classification Search
None
See application file for complete search history.

(56) References Cited

U.S. PATENT DOCUMENTS

| 6,582,908 | B2 * | 6/2003 | Fodor | C12Q 3/00 506/30 |
|---|---|---|---|---|
| 10,308,985 | B2 | 6/2019 | Murphy et al. | |
| 10,787,709 | B2 | 9/2020 | Murphy et al. | |
| 10,941,446 | B2 | 3/2021 | Murphy et al. | |
| 2006/0270612 | A1 | 11/2006 | Blatt et al. | |
| 2007/0269827 | A1 | 11/2007 | Harley | |
| 2008/0319027 | A1 | 12/2008 | Tao et al. | |
| 2009/0022730 | A1 | 1/2009 | Raulf et al. | |
| 2009/0191548 | A1 | 7/2009 | Berlin et al. | |
| 2011/0144914 | A1 | 6/2011 | Harrington et al. | |
| 2011/0171664 | A1 | 7/2011 | O'Brien | |
| 2011/0189680 | A1 | 8/2011 | Keown et al. | |
| 2011/0212090 | A1 | 9/2011 | Pedersen et al. | |
| 2012/0003228 | A1 | 1/2012 | Smith et al. | |
| 2012/0177645 | A1 | 7/2012 | Langermann et al. | |
| 2012/0282696 | A1 | 11/2012 | Johnson et al. | |
| 2012/0321614 | A1 | 12/2012 | Michaud et al. | |
| 2013/0064835 | A1 | 3/2013 | Schmidt | |
| 2013/0078633 | A1 | 3/2013 | Hutchins et al. | |
| 2013/0131194 | A1 | 5/2013 | Skog et al. | |
| 2013/0142728 | A1 | 6/2013 | Beaudenon-Huibregtse et al. | |
| 2013/0143755 | A1 | 6/2013 | Sarwal et al. | |
| 2013/0216533 | A1 | 8/2013 | Bais et al. | |
| 2014/0045915 | A1 | 2/2014 | Skog et al. | |
| 2014/0100124 | A1 | 4/2014 | Wylie et al. | |
| 2014/0141986 | A1 | 5/2014 | Spetzler et al. | |
| 2014/0329704 | A1 | 11/2014 | Melton et al. | |
| 2015/0167085 | A1 | 6/2015 | Salomon et al. | |
| 2017/0114407 | A1 | 4/2017 | Murphy et al. | |
| 2017/0137883 | A1 | 5/2017 | Murphy et al. | |
| 2017/0152560 | A1 | 6/2017 | Murphy et al. | |
| 2018/0068057 | A1 | 3/2018 | Shin et al. | |
| 2018/0356402 | A1 | 12/2018 | Fairchild et al. | |
| 2019/0345556 | A1 | 11/2019 | Murphy et al. | |
| 2021/0230700 | A1 | 7/2021 | Murphy et al. | |

FOREIGN PATENT DOCUMENTS

| CN | 1518458 | 8/2004 |
|---|---|---|
| CN | 101039951 | 9/2007 |
| CN | 101360835 | 2/2009 |
| CN | 102099484 | 6/2011 |
| CN | 102119224 | 7/2011 |
| CN | 102186987 | 9/2011 |
| CN | 102597268 | 7/2012 |

(Continued)

OTHER PUBLICATIONS

NCBI GEO Platform GPL570, Affymetrix Human Genome U133 Plus 2.0 Array, available via URL: < ncbi.nlm.nih.gov/geo/query/acc.cgi?acc=GPL570>, available online Nov. 7, 2003 (Year: 2003).*
Tuttle et al PLoS ONE. Jan. 2014. 9: e87325 (Year: 2014).*
Gokmen-Polar et al. Cancer Research. 2001. 61: 1375-1381 (Year: 2001).*
Haynes et al Electrophoresis. 1998. 19: 1862-1871 (Year: 1998).*
EP Partial Search Report in European Application No. 19789535.2, dated Dec. 6, 2021, 17 pages.
Affymetrix NetAffx Search results, pp. 1-17, accessed Apr. 8, 2021 (Year: 2021).
Alakulppi et al., "Diagnosis of Acute Renal Allograft Rejection by Analyzing Whole Blood mRNA Expression of Lymphocyte Marker Molecules," Transplantation, Mar. 2007, 83: 791-798.
Allanach et al., "Comparing microarray versus RT-PCR assessment of renal allograft biopsies: Similar performance despite different dynamic ranges," American Journal of Transplantation, 2008, 8:1006-1015.

(Continued)

Primary Examiner — Carla J Myers
(74) Attorney, Agent, or Firm — Fish & Richardson P.C.

(57) ABSTRACT

Disclosed herein are gene signature sets expressed by kidney allograft recipients prior to transplant that determine the risk for acute rejection (AR) post-transplant and methods of using the gene signature sets for identifying renal allograft recipients at risk for acute rejection. Also disclosed herein are kits for use in the invention which comprise primer pairs for the gene signature sets.

8 Claims, No Drawings

(56) References Cited

FOREIGN PATENT DOCUMENTS

| | | |
|---|---|---|
| CN | 102666581 | 9/2012 |
| CN | 102712954 | 10/2012 |
| CN | 103025890 | 4/2013 |
| CN | 103421905 | 12/2013 |
| CN | 106461679 | 2/2017 |
| EP | 1374901 | 1/2004 |
| EP | 1731620 | 12/2006 |
| WO | WO 1996/039154 | 12/1996 |
| WO | WO 1997/003211 | 1/1997 |
| WO | WO 2001/081916 | 11/2001 |
| WO | WO 2004/074815 | 9/2004 |
| WO | WO 2007/104537 | 9/2007 |
| WO | WO 2009/143624 | 12/2009 |
| WO | WO 2010/083121 | 7/2010 |
| WO | WO 2011/127219 | 10/2011 |
| WO | WO 2011/143499 | 11/2011 |
| WO | WO 2012/174282 | 12/2012 |
| WO | WO 2013/063322 | 5/2013 |
| WO | WO 2013/063544 | 5/2013 |
| WO | WO 2013/079701 | 7/2013 |
| WO | WO 2013/079791 | 7/2013 |
| WO | WO 2014045915 | 3/2014 |
| WO | WO 2014/071205 | 5/2014 |
| WO | WO 2017/100259 | 6/2017 |
| WO | WO 2017/147196 | 8/2017 |
| WO | WO 2017/203008 | 11/2017 |

OTHER PUBLICATIONS

AU Office Action in Australian Appln. No. 2015229270, dated Jul. 9, 2020, 8 pages.
AU Office Action in Australian Appln. No. 2015279542, dated Aug. 28, 2020, 5 pages.
AU Office Action in Australian Appln. No. 2015279542, dated May 11, 2021, 3 pages.
AU Office Action in Australian Appln. No. 2015279621, dated Aug. 28, 2020, 4 pages.
Ben-Dov et al., "MicroRNA sequence profiles of human kidney allografts with or without tubulointerstitial fibrosis," Transplantation, Dec. 15, 2012, 94(11):1086-1094.
BR Office Action in Brazilian Appln. No. 112016030313-0, dated Dec. 10, 2019, 4 pages (English Translation Only).
BR Office Action in Brazilian Appln. No. 112016030360-1, dated Nov. 29, 2019, 5 pages (English Translation Only).
CA Office Action in Canadian Appln. No. 2942384, dated Mar. 11, 2021, 7 pages.
Chapman, "Do protocol transplant biopsies improve kidney transplant outcomes?," Curr Opin Nephrol Hypertens, Nov. 2012, 21:580-586.
Cheung et al., "Natural variation in human gene expression assessed in lymphoblastoid cells," Nature Genetics, Feb. 3, 2003, 33:422-425.
Cho et al., "Pirfenidone: an anti-fibrotic therapy for progressive kidney disease," Expert Opinion on Investigational Drugs, Feb. 2010, 19(2):275-283.
CN Office Action in Chinese Appln. No. 201580024911.0, dated Dec. 1, 2017, 17 pages (with English Translation).
CN Office Action in Chinese Appln. No. 201580045235.5, dated Jan. 16, 2020, 8 pages (English translation).
CN Office Action in Chinese Appln. No. 201580045324.X, dated Jan. 16, 2020, 7 pages (English translation).
CN Office Action in Chinese Appln. No. 201811063221.8, dated Jun. 1, 2021, 18 pages (with English Translation).
Cobb et al., "Sepsis gene expression profiling: Murine splenic compared with hepatic responses determined by using complementary DNA microarrays," Crit. Care Med., 2002, 30(12):2711-2721.
Cosio et al., "Predicting subsequent decline in kidney allograft function from early surveillance biopsies," American Journal of Transplantation, Oct. 2005,5:2464-2472.

Einecke et al., "A molecular classifier for predicting future graft loss in late kidney transplant biopsies," The Journal of Clinical Investigation, 2010, 120:1862-72.
El-Zoghby et al., "Identifying specific causes of kidney allograft loss," American Journal of Transplantation, Mar. 2009, 9:527-35.
EP Extended European Search Report in European Application No. 15761612.9, dated Aug. 2, 2017, 7 pages.
EP Extended European Search Report in European Application No. 15812651.6, dated Jan. 3, 2018, 9 pages.
EP Extended European Search Report in European Application No. EP110466HV, dated Feb. 1, 2018, 10 pages.
EP Office Action in European Application No. 15811195.5, dated Jul. 9, 2019, 4 pages.
Flechner et al., "Kidney transplant 1,2 rejection and tissue injury by gene profiling of biopsies and peripheral blood lymphocytes," American Journal of Transplantation, Sep. 2004, 4: 1475-1489.
Furness et al., "International variation in histologic grading is large, and persistent feedback does not improve reproducibility," Am J Surg Pathol, Jun. 2003, 27:805-810.
Gorantla et al., "Immunosuppressive agents in transplantation: mechanisms of action and current anti-rejection strategies," Microsurgery, Feb. 2000, 20:420-429.
Hai et al., "Changes of early response gene expression profile of peripheral lymphocytes in human renal allograft recipients," Journal of Clinical Rehabilitative Tissue Engineering Research, 2009, 13(5):841-844 (with English Abstract).
Hayry et al., "Protocol core needle biopsy and histological chronic allograft damage index as surrogate endpoint for Long-Term graft survival," Transplant Proc, Jan.-Feb. 2004, 36:89-91.
Hoshikawa et al., "Hypoxia induces different genes in the lungs of rats compared with mice," Physiol Genomics, Dec. 3, 2002, 12:209-219.
Irizarry et al., "Summaries of Affymetrix GeneChip probe level data," Nucleic Acids Research, 2003, 31:e15.
Isoniemi et al., "Histological chronic allograft damage index accurately predicts chronic renal allograft rejection," Transplantation, Dec. 1994, 58:1195-1198.
Johnson and Li, "Adjusting batch effects in microarray expression data using empirical Bayes methods," Biostatistics, 2007, 8:118-127.
Karczewski et al., "Cytometric analysis of TH1/TH2 cytokines in the urine of patients undergoing kidney transplantation," Annals of Transplantation, 2009, 14(3):25-28.
Kulkarni, Meghana M. "Digital multiplexed gene expression analysis using the NanoString nCounter system," Current Protocols in Molecular Biology, Apr. 1, 2011: 25B-10.1-25B10.17.
Kurtkoti et al., "The utility of 1- and 3-month protocol biopsies on renal allograft function: a randomized controlled study," American Journal of Transplantation, Feb. 2008, 8:317-23.
Li et al., "Fast and accurate short read alignment with Burrows-Wheeler transform," Bioinformatics, 2009, 25(14):1754-1760.
Li et al., "Identification of Common Blood Gene Signatures for the Diagnosis of Renal and Cardiac Acute Allograft Rejection," PLOS One, Dec. 2013, 8: e82153.
Malkov et al. "Multiplexed measurements of gene signatures in different analytes using the Nanostring nCounter Assay System" BMC Research Notes, May 9, 2009 (May 9, 2009), vol. 2, pp. 1-9. entire document.
Maluf et al., "The urine microRNA profile may help monitor post-transplant renal graft function," Kidney International, Jan. 1, 2014, 85(2):439-449.
Mannon et al., "Inflammation in areas of tubular atrophy in kidney allograft biopsies: a potent predictor of allograft failure," American Journal of Transplantation, 2010; 10:2066-73.
Meier-Kriesche et al., "Lack of improvement in renal allograft survival despite a marked decrease in acute rejection rates over the most recent era," American Journal of Transplantation, Jan. 2004, 4:378-83.
Mengel et al., "Banff 2011 Meeting report: new concepts in antibody-mediated rejection," American Journal of Transplantation, 2012, 12:563-570.

(56) References Cited

OTHER PUBLICATIONS

Menon et al., "Moving biomarkers toward clinical implementation in kidney transplantation," Journal of the American Society of Nephrology, 2017, 28:735-747.
Metzker, "Sequencing technologies—the next generation," Nature Reviews Genetics, Jan. 2010, 11:31-46.
Miller et al., "A new method for stranded whole transcriptome RNA-seq," Methods, 2013, 63(2):126-134.
Morgun et al., "Molecular profiling improves diagnoses of rejection and infection in transplanted organs," Circulation Research, 2006, 98(12):e74-e83.
Mueller et al., "Microarray analysis of rejection in human kidney transplants using pathogenesis-based transcript sets," American Journal of Transplantation., 2007, 7(2):2712-2722.
Naesens et al., "Progressive histological damage in renal allografts is associated with expression of innate and adaptive immunity genes," Kidney International, Dec. 2011,80:1364-76.
Nankivell et al., "Effect of histological damage on long-term kidney transplant outcome," Transplantation, Feb. 2001, 71:515-523.
Nankivell et al., "The natural history of chronic allograft nephropathy," N Engl J Med, 2003, 349:2326-33.
Nguyen et al. "Molecular Mechanisms Involved in Calcineurin Inhibitor Nephrotoxicity in Kidney Allograft Transplants," Master's Thesis, Virginia Commonwealth University, Aug. 8, 2011 (Aug. 8, 2011), pp. 1-74. Retrieved from the Internet< ttp://scholarscompass.vcu.edu/etd/2545/> on May 7, 2015 (May 7, 2015). entire document.
Omran et al., "MicroRNAs: New Insights into Chronic Childhood Diseases," BioMed Research International, Jul. 7, 2013, 2013:13 pages.
Park et al., "Fibrosis with inflammation at one year predicts transplant functional decline," J Am Soc Nephrol, 2010, 21:1987-97.
PCT International Preliminary Report on Patentability in International Application No. PCT/US2015/038147, dated Dec. 27, 2016, 10 pages.
PCT International Preliminary Report on Patentability in International Appln. No. PCT/US2019/027618, dated Oct. 20, 2020, 9 pages.
PCT International Search Report and Written Opinion in International Appln. No. PCT/US2015/020291, dated Jun. 11, 2015, 15 pages.
PCT International Search Report and Written Opinion in International Appln. No. PCT/US2019/027618, dated Jul. 10, 2019, 12 pages.
PCT International Search Report and Written Opinion in International Appln. No. PCT/US2015/038171, dated Dec. 8, 2015, 15 pages.
PCT International Search Report and Written Opinion in International Appln. No. PCT/US2015/038147, dated Oct. 23, 2015, 11 pages.
Ritchie et al., "limma powers differential expression analyses for RNA-sequencing and microarray studies," Nucleic Acids Research, 2015, 43(7):e47.
Rush et al., "Beneficial effects of treatment of early subclinical rejection: a randomized study," J Am Soc Nephrol, 1998, 9:2129-34.
Rush et al., "Lack of benefit of early protocol biopsies in renal transplant patients receiving TAC and MMF: a randomized study," American Journal of Transplantation, Nov. 2007, 7:2538-45.
Schadt et al., "A window into third-generation sequencing," Human Molecular Genetics, Sep. 21, 2010, 19(2):R227-R240.
Scherer et al., "Transcriptome changes in renal allograft protocol biopsies at 3 months precede the onset of interstitial fibrosis/tubular atrophy (IF/TA) at 6 months," Nephrol Dial Transplant, 2009, 24:2567-75.
Schwarz et al., "Safety and adequacy of renal transplant protocol biopsies," American Journal of Transplantation, Aug. 2005, 5:1992-6.
Seron et al., "Early protocol renal allograft biopsies and graft outcome," Kidney Int, Jan. 1997, 51:310-316.
Seron et al., "Reliability of chronic allograft nephropathy diagnosis in sequential protocol biopsies," Kidney Int, 2002, 61:727-33.
Shendure et al., "Next-generation DNA sequencing," Nature Biotechnology, 2008, 26(10):1135-1145.
Shishido et al., "The impact of repeated subclinical acute rejection on the progression of chronic allograft nephropathy," J Am Soc Nephrol, 2003, 14:1046-52.
Solez et al., "Banff 07 classification of renal allograft pathology: updates and future directions," American Journal of Transplantation, 2008, 8:753-760.
Spector et al., "Development And Validation Of A MicroRNA-Based Diagnostic Assay For Classification Of Renal Cell Carcinomas," Molecular Oncology, Mar. 26, 2013, 7:732-738.
Spivey et al., "Gene expression profiling in acute allograft rejection: challenging the immunologic constant of rejection hypothesis," Journal of Translational Medicine, 2011, 9:1-22.
Stegall et al., "The histology of solitary renal allografts at 1 and 5 years after transplantation," American Journal of Transplantation, Apr. 2011, 11:698-707.
Subramanian et al., "Gene set enrichment analysis: a knowledge-based approach for interpreting genome-wide expression profiles," PNAS, Oct. 2005, 102:15545-50.
Wolfe et al., "Trends in organ donation and transplantation in the United States, 1999-2008," American Journal of Transplantation, Apr. 2010, 10:961-72.
Yilmaz et al., "Clinical predictors of renal allograft histopathology: a comparative study of single-lesion histology versus a composite, quantitative scoring system," Transplantation, Mar. 2007, 83:671-676.
Yilmaz et al., "Protocol core needle biopsy and histologic Chronic Allograft Damage Index (CADI) as surrogate end point for long-term graft survival in multicenter studies," Journal of the American Society of Nephrology, 2003, 14:773-779.
Zhang et al., "Pretransplant transcriptomic signature in peripheral blood predicts early acute rejection," JCI Insight. 2019, 4(11):e127543.
CA Office Action in Canadian Appln. No. 2942384, dated Jan. 14, 2022, 5 pages.
Alakulppi et al., "Diagnosis of Acute Renal Allograft Rejection by Analyzing Whole Blood mRNA Expression of Lymphocyte Marker Molecules," Transplantation, Mar. 2007, 83(6):791-798.
Bontadini, "HLA techniques: Typing and antibody detection in the laboratory of immunogenetics," Methods, Apr. 2012, 56(4):471-576.
BR Office Action in Brazilian Appln. No. 112016020987-7, dated Oct. 8, 2019, 5 pages (English Translation Only).
CA Office Action in Canadian Appln. No. 2953368, dated May 4, 2021, 4 pages.
CA Office Action in Canadian Appln. No. 2953369, dated May 3, 2021, 4 pages.
Chen et al., "Changes of early response gene expression profile of peripheral lymphocytes in human renal allograft recipients," Journal of Clinical Rehabilitative Tissue Engineering Research, Jan. 29, 2009, 13(5):841-844 (with English abstract).
CN Office Action in Chinese Appln. No. 201580045324.X, dated Dec. 24, 2020, 10 pages (with English translation).
EP Office Action in European Application No. 15812651.6, dated Oct. 10, 2019, 5 pages.
Hurvich et al., "A Corrected Akaike Information Criterion for Vector Autoregressive Model Selection," Journal of Time Series Analysis, 2008, 14:271-279.
Ihaka, "R: A Language for Data Analysis and Graphics," Journal of Computational and Graphical Statistics, Sep. 1996, 5(3):299-314.
Li et al., "The Sequence Alignment/Map format and SAMtools," Bioinformatics. Aug. 2009; 25(16): 2078-2079.
Mata et al., "A Hexameric Phosphorothioate Oligonucleotide Telomerase Inhibitor Arrests Growth of Burkitt's Lymphoma Cells in Vitro and in Vivo," Toxicology Applied Pharmacology, May 1997, 144:189-197.
Mootha et al., "PGC-1 alpha-responsive genes involved in oxidative phosphorylation are coordinately downregulated in human diabetes," Nat Genet, 2003, 34:267-273.

(56) References Cited

OTHER PUBLICATIONS

Samstag et al., "Synthesis and Properties of New Antisense Oligodeoxynucleotides Containing Benzylphosphonate Linkages," Antisense Nucleic Acid Drug Development, 1996, 6:153-156.
Strauss-Soukup et al., "Effects of Neutralization Pattern and Stereochemistry on DNA Bending by Methylphosphonate Substitutions," Biochemistry, Jul. 1997, 36:8692-8698.
Tibshirani et al., "Regression Shrinkage and Selection via the Lasso," Journal of the Royal Statistical Society Series B, 1996, 58:267-288.
Tran et al., "Inferring causal genomic alterations in breast cancer using gene expression data," BMC Sy st Biol, Aug. 2011, 5:121.
Trapnell et al., "Differential gene and transcript expression analysis of RNA-seq experiments with TopHat and Cufflinks," Nat Protoc, Mar. 2012, 7:562-578.
Vahed et al., "Diagnosis of Interstitial Fibrosis and Tubular Atrophy in Kidney Allograft: Implementation of MicroRNAs ", Iranian Journal of Kidney Diseases, Jan. 2014, 8(1):4-12.
Zhu et al., "Integrating large-scale functional genomic data to dissect the complexity of yeast regulatory networks," Nat Genet, Jul. 2008, 40:854-861.
CA Office Action in Canadian Appln. No. 2953369, dated Apr. 6, 2022, 3 pages.
EP Extended European Search Report in European Application No. 19789535.2, dated Mar. 10, 2022, 16 pages.
U.S. Appl. No. 15/125,009, filed Sep. 9, 2016, Barbara Murphy.
U.S. Appl. No. 17/164,607, filed Feb. 1, 2021, Barbara Murphy.
U.S. Appl. No. 15/321,885, filed Dec. 23, 2016, Barbara Murphy.
U.S. Appl. No. 15/320,208, filed Dec. 19, 2016, Barbara Murphy.
U.S. Appl. No. 16/424,014, filed May 28, 2019, Barbara Murphy.

\* cited by examiner

METHOD FOR PREDICTION OF ACUTE REJECTION AND RENAL ALLOGRAFT LOSS USING PRE-TRANSPLANT TRANSCRIPTOMIC SIGNATURES IN RECIPIENT BLOOD

TECHNICAL FIELD

This invention relates to the field of molecular biology, and more particularly to detecting mRNA molecular signatures. More particularly, this invention relates to methods for diagnosing a renal allograft recipient's risk for developing acute rejection and allograft loss. The methods comprise analyzing the blood of renal allograft recipients by determining the expression level of an mRNA signature set comprising 23 preselected mRNAs in order to identify and treat such patients pre- and post-transplantation. A differential expression analysis can be applied to normalized expression read count (e.g. read counts of genes from next generation sequencing technology) values of selected genes to derive a weighted cumulative risk score for the risk of acute rejection and allograft loss which can be obtained for each patient.

BACKGROUND OF THE INVENTION

Kidney transplantation is the treatment of choice for subjects with end stage renal disease (ESRD). However, despite remarkable improvements in 1-year graft loss over the last decade, in each subsequent year after transplant, approximately 3% of kidney allograft recipients return to dialysis or require re-transplantation. Though recent data may indicate an uptick in intermediate-term graft loss since 2006 associated with better renal function, rates of late graft failure are relatively unchanged since the 1990s.

Chronic allograft damage, or interstitial fibrosis and tubular atrophy of unknown cause account for most of the cases of graft loss. This has boosted research aimed at understanding and contrasting the mechanisms responsible for these late events, including, among others, alloantibody formation and recurrence of primary disease. Indeed, lack of long-term improvements despite dramatic reduction of acute rejection has challenged the assumption that acute rejection represents a major determinant of long term graft outcomes. This assumption, however, contrasts with evidence that early acute rejection (EAR,) with an inflammation/tubulitis score of 1 or above based on kidney biopsies obtained before 6 months after transplant, both clinically manifested and subclinical, negatively impacts long-term graft loss in patients receiving current immunosuppressive regimens. Therefore, EAR still represents one of the major targets for immunosuppressive therapy after transplantation.

One of the major issues of current immunosuppressive protocols is the fact that they are not tailored to the single patient needs. Current clinical practice depends on broad clinical criteria including anti-HLA antibodies, race, prior transplantation and recipient age to predict individual immunological risk post-transplantation. These indicators perform poorly. As a result, most patients receive a standardized immunosuppressive protocol resulting in some individuals being exposed to too much or too little immunosuppression, with resultant complications. Early identification of individuals at highest risk of acute rejection could allow targeted therapies aimed at improving long-term outcomes.

Evidence exists that the composition and function of the immune system in patients prior to renal transplantation affects the risk for subsequent acute rejection (AR) after transplantation, but no biomarker has been identified to quantify this risk. What is needed are gene signature sets that can be used for transcript profiling of patients' blood prior to renal transplant to predict acute rejection episodes.

SUMMARY OF THE INVENTION

The present inventors have identified and validated a blood based 23-gene set in allograft recipients prior to transplant that predicts the risk of EAR and is associated with late AR and allograft loss. Application of this gene set allows the immune stratification of transplant patients prior to transplantation, thereby allowing an individualized approach to immunosuppressive therapy.

Disclosed herein are gene profiles expressed by kidney allograft recipients prior to transplant that determine the risk for acute rejection (AR) post-transplant.

In one aspect, the present invention provides a method for identifying a renal allograft recipient at risk of developing acute rejection comprising the steps of (a) determining the expression levels of genes in a gene signature set in a blood specimen obtained from the recipient; (b) comparing the expression levels of the genes in the gene signature set with the expression levels of the same genes in the gene signature set in a control gene set, and (c) determining the recipient will be at risk for acute rejection and allograft loss if the expression level of one or more genes in the gene signature set in the specimen is altered compared to the expression level of the same one or more genes in the gene signature set in the control.

In another aspect, the gene expression level results of the assay are applied to summarize as a weighted cumulative score (r) the risk of EAR. The formula employed for the risk assessment is $r = -(\log 10(p1)*g1 + \log 10(p2)*g2 + \ldots + \log 10(pi)*gi + \ldots + \log 10(p23)*g23)$, where pi is the significance p value of t-test on expression values for gene i (i=1 ... 23) between the EAR vs the non-EAR groups in the training set, gi is a logic number for gene i (i=1 ... 23), 1 (if the expression value of gene i is greater than the median expression value of the EAR group of the training set for an upregulated gene or if the expression value of gene i is less than the median expression value of the non-EAR group of the training set for a downregulated gene), or −1 (if the expression value of gene i is less than the median value of the non-EAR group of the training set for an upregulated gene or if the expression value of gene i is greater than the median value of the non-EAR group of the training set for a downregulated gene), or 0 (if the expression value of gene i is between the median values of the EAR and the non-EAR groups of the training set). The weighted cumulative score (r) can be used as a risk score for acute rejection for each patient. If the risk score of the patient is higher than the tertile expression value cutoffs defined from the training dataset, then the patient is at risk for acute rejection.

In another aspect, the present invention provides a kit for identifying renal allograft recipients that are at risk for acute rejection comprising in one or more separate containers primer pairs for the gene signature set: GZMH, ADGRG1, S1PR5, FGFBP2, NKG7, PRF1, KIAA1671, LAG3, TARP, FCRL6, FASLG, TBX21, TOX, ZNF831, CD8A, C1orf21, CCR5, LDOC1L, CCDC102A, HOPX, PRKCH, SLC25A34, F12, buffers, a housekeeping gene panel, primers for the housekeeping gene panel, negative controls and instructions for use.

In yet another aspect, the present invention provides a method for identifying a renal allograft recipient at risk of acute rejection of the allograft before transplantation comprising the steps of (a) isolating mRNA from a blood specimen from the renal allograft recipient (b) synthesizing cDNA from the mRNA; (c) determining the expression levels of the 23 member gene signature set in said recipient's blood; and (d) diagnosing the allograft recipient as being at risk for acute rejection and allograft loss if the weighted cumulative risk score (r) calculated from the expression levels of the 23-member gene set is higher than the tertile cutoff and (e) treating the recipient identified as being at risk for acute rejection or allograft loss with induction therapy or administering higher maintenance immunosuppression such as higher target doses of calcineurin inhibitors.

In yet another aspect the present invention provides a method for treating patients who are at low risk for acute rejection and/or graft loss comprising administering lower risk maintenance immunosuppression such as rapaymycin or belatacept, thereby decreasing the risk for infection and malignancy.

In yet a still further aspect, the present invention provides a method for selecting a renal allograft patient for induction therapy prior to transplantation to reduce the risk of renal acute rejection or allograft loss which comprises comparing the expression levels of the 23 member gene signature set obtained from the patient with the expression level of the same gene signature set in a control sample obtained from an allograft recipient that did not suffer acute rejection, and treating the patient with induction therapy if the expression level of one or more genes in the gene signature set from the patient is altered compared to the expression level of the same one or more genes in the gene signature set in the control.

These and other aspects of the present invention will be apparent to those of ordinary skill in the art in light of the present specification and appended claims.

DETAILED DESCRIPTION OF THE INVENTION

Definitions

As used herein, an allograft recipient who is at "high risk" for acute rejection of the allograft and allograft loss is significantly more likely to reject the allograft, without intervention, than a subject who is at "low risk."

In accordance with the present invention, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4th ed. Wiley-Liss; among others. The Current Protocols listed above are updated several times every year.

As used herein, the "expression level" of an mRNA disclosed herein means the mRNA expression level of the marker, or the measurable level of the marker in a sample, which can be determined by any suitable method known in the art, such as, but not limited to Northern blot, polymerase chain reaction (PCR), e.g., quantitative real-time PCR, "qRT-PCR", RNA-seq, TREex (miSEQ), Nanostring analysis, etc. As used herein, the term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude) preferably within a factor of two of a given value.

The terms "decrease", "decreased", "reduced", "reduction" or "down-regulated" are all used herein generally to mean a decrease by a statistically significant amount. However, for avoidance of doubt, "reduced", "reduction", "down-regulated" "decreased" or "decrease" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold decrease, or any decrease between 1.0-fold and 10-fold or greater as compared to a reference level.

The terms "increased", "increase" or "up-regulated" are all used herein to generally mean an increase by a statistically significant amount; for the avoidance of any doubt, the terms "increased" or "increase" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold increase, or any increase between 1.0-fold and 10-fold or greater as compared to a reference level.

As used herein, "determining the level of expression," "determining the expression level" or "detecting the level of expression", as in, for example, "determining the expression level of a gene" refers to quantifying the amount of mRNA present in a sample. Detecting expression of the specific mRNAs can be achieved using any method known in the art as described herein. Typically, mRNA detection methods involve sequence specific detection, such as by RT-PCR. mRNA specific primers and probes can be designed using nucleic acid sequences, which are known in the art.

As used herein, an "altered" level of expression of a mRNA compared to reference level or control level is an at least 0.5-fold (e.g., at least: 1-; 2-; 3-; 4-; 5-; 6-; 7-; 8-; 9-; 10-; 15-; 20-; 30-; 40-; 50-; 75-; 100-; 200-; 500-; 1,000-; 2000-; 5,000-; or 10,000-fold) altered level of expression of the mRNA. It is understood that the alteration can be an increase or a decrease. Alternatively, altered expression level is defined as an increase in the risk probability score using parameters in the logistic regression model established from a training patient group, comparing the probability score to the cutoff derived from the training set.

As used herein "combination therapy" means the treatment of a subject in need of treatment with a certain composition or drug in which the subject is treated or given one or more other compositions or drugs for the disease in conjunction with the first and/or in conjunction with one or more other therapies, such as, e.g., an immunosuppressive therapy or other anti-rejection therapy. Such combination therapy can be sequential therapy wherein the patient is treated first with one treatment modality (e.g., drug or therapy), and then the other (e.g., drug or therapy), and so on, or all drugs and/or therapies can be administered simultaneously. In either case, these drugs and/or therapies are said to be "co-administered." It is to be understood that "co-administered" does not necessarily mean that the drugs and/or therapies are administered in a combined form (i.e., they may be administered separately or together to the same or different sites at the same or different times).

The term "pharmaceutically acceptable derivative" as used herein means any pharmaceutically acceptable salt, solvate or prodrug, e.g., ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol. 1: Principles and Practice, which is incorporated herein by reference to the extent of teaching such derivatives. Pharmaceutically acceptable derivatives include salts, solvates, esters, carbamates, and/or phosphate esters.

As used herein the terms "therapeutically effective" and "effective amount", used interchangeably, applied to a dose or amount refer to a quantity of a composition, compound or pharmaceutical formulation that is sufficient to result in a desired activity upon administration to a subject in need thereof. Within the context of the present invention, the term "therapeutically effective" refers to that quantity of a composition, compound or pharmaceutical formulation that is sufficient to reduce or eliminate at least one symptom of a disease or condition specified herein, e.g., acute rejection and/or allograft rejection when a combination of active ingredients is administered, the effective amount of the combination may or may not include amounts of each ingredient that would have been effective if administered individually. The dosage of the therapeutic formulation will vary, depending upon the nature of the disease or condition, the patient's medical history, the frequency of administration, the manner of administration, the clearance of the agent from the host, and the like. The initial dose may be larger, followed by smaller maintenance doses. The dose may be administered, e.g., weekly, biweekly, daily, semi-weekly, etc., to maintain an effective dosage level.

"Control" is defined as a sample obtained from a patient that received an allograft transplant that is not suffering from acute rejection.

"Induction therapy" is defined herein as administration of an immunosuppressive agent to a patient at high risk of acute rejection begun before or preferably on the day of the transplant. The agent is a biologic agent, either a lymphocyte-depleting agent or an interleukin 2-receptor antagonist (IL2-RA) as described below. The purpose of induction therapy is to deplete or modulate T-cell responses in patients at high risk for acute rejection at the time of transplantation and reduce the risk for acute rejection.

As used herein, early acute rejection (EAR) is defined as rejections occurring before 6 months post transplantation.

Pursuant to the present invention, a patient that is being evaluated for renal transplant will have the assay of the present invention performed as part of their pre-transplant evaluation. Peripheral blood will be taken, mRNA will be extracted and TRex (miSEQ) will be performed using reagents and primers for targeted amplification and sequencing library generation. This assay performs targeted sequencing of the specific 23 genes and the housekeeping gene panels. Expression levels will be determined for the 23 genes and the risk algorithm will be applied to determine the risk assessment score for the patients at risk for acute rejection after transplantation. If the patient's score is above 32 the patient is categorized as being at high risk, in which case the patient will receive induction therapy and maintenance immunosuppression that will be managed in the same manner employed for a high risk patient e.g., slower taper of immunosuppressive drugs such as calcineurin inhibitors (CNI's), avoidance of steroid withdrawal, avoidance of mTOR inhibitors (such as Sirolimus/Temsirolimus or Everolimus) or Belatacept. If the score is below −23 the patient is regarded as being at a low risk for AR, in which case the patient would not require induction therapy or they may be a candidate for steroid withdrawal, mTOR inhibitors or Belatacept. The exact cutoffs are based on TRex (miSEQ) assay and will vary based on other technologies, such as Nanostring and qPCR. Of note, the assay should be taken in the context of other clinical factors that would predefine a candidate as high risk e.g., HLA match and the presence of anti-HLA-antibodies, when planning the immunosuppression protocol for the patient.

The present invention is based on the identification of gene expression profiles expressed by a kidney allograft recipient prior to transplant that determine the risk for acute rejection post-transplant. The gene expression profile is predictive of subclinical as well as clinical acute rejection post-transplantation. This gives the clinician the ability to personalize the approach to the immunosuppression regimen at the time of the transplant, thereby maximizing immunosuppression in those at high risk and lowering immunosuppression in those with decreased risk. Specifically, induction therapy using, for example thyroglobulin/Anti-Thymocyte Globulin (ATG), or an anti-IL-2R blocker or Campath-1H (Alemtuzmab, or an anti-CD52 monoclonal antibody directed against an antigen present on the surface of T lymphocytes) will be administered to patients at high risk for acute rejection and avoided in patients at low risk for acute rejection. Induction therapy is started the day of the transplant. For maintenance immunosuppression, an individual at lower risk can, depending on other immunological factors, can be treated with a weaker immunosuppressant, such as Rapamycin or Belatacept. These are recognized by those of ordinary skill in the art as less potent because they are associated with a high acute rejection rate. "Stronger" immunosuppressive agents include CNI's, such as tacrolimus (Prograf® and Advagraf®/Astagraf XL (Astellas Pharma Inc.) and generics of Prograf® and cyclosporine (Neoral® and Sandimmune® (Novartis AG) and generics.

In addition, decisions regarding the donor/recipient combination may be guided so as to minimize other controllable immunological factors. For example, transplantations could be avoided based on donor/recipient combinations in which the recipient has antibodies directed against the donor HLA.

In this embodiment, transplantation may be avoided if a patient required desensitization, i.e., plasmapheresis and intravenous immunoglobulin (IVIG) administration for donor specific antibodies. However, this would mostly apply to living donor allografts. In this embodiment, avoiding donor/recipient mismatches can result in significant cost savings.

In addition, if the gene expression profile identifies an individual as at risk for acute rejection, the patient may be subjected to more intensive monitoring of clinical laboratory results or gene expression profiles for diagnosing subclinical acute rejection.

The present invention provides methods for identifying kidney allograft recipients at risk for acute rejection and graft loss prior to transplantation comprising the steps of providing a blood specimen from a kidney allograft recipient before transplantation, isolating mRNA from the blood specimen, synthesizing cDNA from the mRNA, and measuring the expression levels of a 23 member gene signature set present in the blood specimen. Non-limiting examples of methods of measuring expression levels include the RNA-seq, targeted RNA expression (TREx) sequencing system (Illumina, Inc. San Diego Calif.), Nanostring (nCounter® mRNA Expression Assay-Nanostring Technologies, Inc. Seattle Wash.) or qPCR. The results of the gene signature set analysis are compared to a control. The greater the alteration in patient's expression level compared to the control, the greater the risk of acute rejection. These methods are described in Examples 1-6 below.

Peripheral blood signatures using gene signature sets comprising 23 preselected genes have been identified. These preselected gene signature sets can be used to accurately identify kidney allograft recipients at risk for acute rejection and subsequent graft rejection before the transplant surgery.

The 23 member gene signature set for use in practicing the methods disclosed herein comprises the following genes: GZMH, ADGRG1, S1PR5, FGFBP2, NKG7, PRF1, KIAA1671, LAG3, TARP, FCRL6, FASLG, TBX21, TOX, ZNF831, CD8A, C1orf21, CCR5, LDOC1L, CCDC102A, HOPX, PRKCH, SLC25A34 and F12.

In this context, it has been found that if the allograft recipient is at low risk for acute rejection but they have 5 or 6 HLA mismatches they become high risk for acute rejection. HLA typing can be done by flow cytometry, RT-PCR and RNA-Seq. (Reference: Methods. 2012 April; 56(4):471-6. doi: 10.1016/j.ymeth.2012.03.025. Epub 2012 Mar. 28. HLA techniques: typing and antibody detection in the laboratory of immunogenetics. Bontadini A.).

In some of the methods disclosed herein, it is desirable to detect and quantify mRNAs present in a sample. Detection and quantification of RNA expression can be achieved by any one of a number of methods well known in the art. Using the known sequences for RNA family members, specific probes and primers can be designed for use in the detection methods described below as appropriate. Any one of Nanostring, RNAseq, or quantitative Polymerase Chain Reactions (qPCR) such as Real Time Polymerase Chain Reactions (RT-PCR) or Targeted RNA sequencing (TREx) can be used in the methods disclosed herein. In some cases, detection and quantification of RNA expression requires isolation of nucleic acid from a sample, such as a cell or a tissue. Nucleic acids, including RNA and specifically mRNA, can be isolated using any suitable technique known in the art. For example, phenol-based extraction is a common method for isolation of RNA. Phenol-based reagents contain a combination of denaturants and RNAase inhibitors for cell and tissue disruption and subsequent separation of RNA from contaminants. In addition, extraction procedures such as those using TRIZOL™ or TRI REAGENT™, will purify all RNAs, large and small, and are efficient methods for isolating total RNA from biological samples that contain mRNAs. Extraction procedures such as those using the QIAGEN-ALL prep kit are also contemplated.

In some embodiments, use of quantitative RT-PCR is desirable. Quantitative RT-PCR is a modification of the polymerase chain reaction method used to rapidly measure the quantity of a nucleic acid. qRT-PCR is commonly used for the purpose of determining whether a genetic sequence is present in a sample, and if it is present, the number of copies in the sample. Any method of PCR that can determine the expression of a nucleic acid molecule, including an mRNA, falls within the scope of the present invention. There are several variations of the qRT-PCR method that are well known to those of ordinary skill in the art. In some embodiments, the mRNA expression profile can be determined using an nCounter® analysis system (NanoString Technologies®, Seattle, Wash.). The nCounter® Analysis System from NanoString Technologies profiles hundreds of mRNAs, microRNAs, or DNA targets simultaneously with high sensitivity and precision. Target molecules are detected digitally. The NanoString analysis system uses molecular "barcodes" and single-molecule imaging to detect and count hundreds of unique transcripts in a single reaction. The protocol does not include any amplification steps. This is a preferred method for rapid detection of the expression levels of mRNAs.

In another embodiment, the invention provides kits for determining whether a patient that will receive a kidney allograft is at risk for acute rejection of the allograft comprising in one or more containers primer pairs for the 23 gene signature set, positive and negative controls, buffers and printed instructions for use. The kits can also contain housekeeping gene panels to test the quality of the assays and primers for the housekeeping genes. The housekeeping gene panels are described in Example 6 below.

In a typical embodiment, a clinical lab will obtain the expression value using the patient's blood sample and send it to the patient's doctor. The doctor will then communicate this value to his web based service provider. The service provider will enter that value in the bioinformatics system which already has the p value weighted parameter and the median expression value for the EAR and non-EAR groups for each gene of the preselected gene signature set and the tertile cutoffs defined from the training set. The bioinformatics system will use this information to calculate the risk score for the patient. The calculated risk score will reflect the patient's AR status.

In an alternate embodiment, the assay will be done centrally in one lab and the results will be sent directly to the doctor i.e., no web based application.

A non-limiting example of the use of the gene signature set in predicting the risk for AR is described below using the 23 gene signature set.

1) Selecting a training group: A group of kidney transplant patients with known Early Acute Rejection (EAR, inflammation/tubulitis score of 1 or above before 6 month after transplant) and a non-EAR control, (with an inflammation/tubulitis score of 0 before 6 month after transplant, diagnosis based on pathology; total number N=~100) will be carefully selected. The training group will have well-characterized demographics, clinical data, and pathological results which will be reviewed by at least two pathologists. The gene expression levels of the training set is used to derive the p value and median expression value in the EAR or non-EAR group for risk score calculation for each gene.

2) Measuring the expression of the genes: Expression levels of the 23 genes from the blood samples pre-transplant of each patient in the training group will be measured using any one of several well-known techniques, and preferably by using TREx, RT-PCR or Nanostring technology. Use of the TREx, Nanostring or qPCR techniques is described in Examples 2, 3 and 4 below. The expression level is represented differently based on the technology applied. TREx uses the count of sequence reads that are mapped to the genes. qPCR uses CT (cycle time) values and Nanostring uses the count of the transcripts.

3) Establishing a cumulative risk score and cutoff: The differential expression analysis will be performed to compute the p value of the difference of the expression values between the EAR and the non-EAR groups for each gene in the training set as described above and the weighted cumulative score will be determined for each patient. The formula employed for the risk assessment is $r=-(\log_{10}(p_1)*g_1+\log_{10}(p_2)*g_2+ \ldots +\log_{10}(p_{23})*g_{23})$, where $p_i$ is the significance p value of t-test on expression values for gene i (i=1 . . . 23) between the EAR vs the non-EAR groups in the training set, $g_i$ is a logic number for gene i (i=1 . . . 23), 1 (if the expression value of gene i is greater than the median expression value of the EAR group of the training set for an upregulated gene or if the expression value of gene i is less than the median expression value of the EAR group of the training set for a downregulated gene), or −1 (if the expression value of gene i is less than the median value of the non-EAR group of the training set for an upregulated gene or if the expression value of gene i is greater than the median value of the non-EAR group of the training set for a downregulated gene), or 0 (if the expression value of gene i is between the median values of the EAR and the non-EAR groups of the training set)

Based on the risk score, the prediction statistics such as prediction AUC (area under the curve) of the ROC (Receiver operating characteristic) curve of the true positive rate versus the false positive rate at various threshold settings are obtained. ROC analysis can be used to determine the cutoff or optimal model and measure the overall prediction accuracy by calculation of the area under the curve, sensitivity/specificity, the positive predictive values (PPV) and the negative predictive values (NPV). At a given specificity (90%), a risk score cutoff will be established which best detects the presence of acute rejection. It is expected that there will be a clear cutoff into two groups in that if a patient is in the top group they have a high likelihood of having acute rejection and the test is determined to be positive but if they are in the bottom group they have a very low likelihood of having acute rejection and the test is determined to be negative.

Alternatively, patients are broken into tertiles based on their probability score determined as above. In this case if the patient is in (1) the top tertile they have a high likelihood of having acute rejection and the test is determined to be positive; (2) the second tertile or intermediate group their risk cannot be accurately determined; and (3) the bottom tertile they have a very low likelihood of having acute rejection (and therefore are a good candidate for successful transplant) and the test is determined to be negative.

The p value, the median expression values of the EAR and non-EAR groups for each gene and the risk score cutoffs derived from the training group are entered and stored into a web-based bioinformatics computer system which can be accessed from a clinical lab/or a doctor office via the internet.

4) Diagnosis: The expression levels of the gene signature sets for a new patient with unknown diagnosis are measured by the same technology used for the training set in the clinical lab. By using a web-based bioinformatics system, the risk score will be calculated by summarizing the expression logic value (1, 0, or −1) compared to the median values of the EAR and non-EAR groups of the 23 genes multiplied by log p values derived from the training set. The risk score is compared to the cutoff to determine the AR status. An increase in the risk score in the patient relative to the risk score in a control indicates that the patient is at an increased risk for acute rejection. A clinical lab will send the testing results to the doctor.

Expression levels and/or reference expression levels may be stored in a suitable data storage medium (e.g., a database) and are, thus, also available for future diagnoses. This also allows for efficiently diagnosing the prevalence of a disease because suitable reference results can be identified in the database once it has been confirmed (in the future) that the subject from which the corresponding reference sample was obtained did experience acute rejection.

As used herein a "database" comprises data collected (e.g., analyte and/or reference level information and/or patient information) on a suitable storage medium. Moreover, the database may further comprise a database management system. The database management system is, preferably, a network-based, hierarchical or object-oriented database management system. More preferably, the database will be implemented as a distributed (Federal) system, e.g. as a Client-Server-System. More preferably, the database is structured as to allow a search algorithm to compare a test data set with the data sets comprised by the data collection. Specifically, by using such an algorithm, the database can be searched for similar or identical data sets being indicative of renal allograft rejection risk. Thus, if an identical or similar data set can be identified in the data collection, the test data set will be associated with renal allograft rejection risk.

Consequently, the information obtained from the data collection can be used to diagnose an allograft recipient's risk for allograft loss or based on a test data set obtained from a subject. More preferably, the data collection comprises characteristic values of all analytes comprised by any one of the groups recited above.

The invention further provides for the communication of assay results or diagnoses or both to technicians, physicians or patients for example. In certain embodiments, computers will be used to communicate assay results or diagnoses or both to interested parties, e.g., physicians and their patients.

In some embodiments, the method disclosed herein further comprises modifying the recipient's clinical record to identify the recipient as being at risk for developing acute rejection and/or allograft loss. The clinical record may be stored in any suitable data storage medium (e.g., a computer readable medium).

In some embodiments of the invention, a diagnosis based on the methods provided herein is communicated to the allograft recipient as soon as possible after the diagnosis is obtained. The diagnosis may be communicated to the recipient by the recipient's treating physician. Alternatively, the diagnosis may be sent to a recipient by e-mail or communicated to the subject by phone. The diagnosis may be sent to a recipient in the form of a report. A computer may be used to communicate the diagnosis by e-mail or phone. In certain embodiments, the message containing results of a diagnostic test may be generated and delivered automatically to the recipient using a combination of computer hardware and software which will be familiar to artisans skilled in telecommunications.

Aspects of the present invention include computer program products for identifying a subject who has not undergone a renal allograft and is at risk for acute rejection, wherein the computer program product, when loaded onto a computer, is configured to employ a gene expression result from a sample derived from the subject to determining whether a subject who will undergo a renal allograft is at risk for acute rejection wherein the gene expression result comprises expression data for at least one gene signature set.

Also provided are reference expression profiles for a phenotype that is one of: (a) low risk for acute rejection; or (b) high risk for acute rejection; wherein the expression profile is recorded on a computer readable medium that is accessible by a user, e.g., in a user readable format. In certain embodiments, the expression profile is a profile for a phenotype that is low risk. In certain embodiments, the expression profile is a profile for a phenotype that is high risk.

The expression profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a user employing a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of ordinary skill in the art can readily appreciate how any of the presently known computer readable mediums can be used to create a manufacture comprising a recording of the present database information.

"Recorded" refers to a process for storing information on computer readable medium, using any such methods known in the art. Any convenient data storage structure may be chosen, based on the means used to access the stored information. A variety of data processor programs and formats can be used for storage, e.g. word processing text file, database format, etc. Thus, the subject expression profile databases are accessible by a user, i.e., the database files are saved in a user-readable format (e.g., a computer readable format, where a user controls the computer).

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

Kits

In certain embodiments, kits are provided for determining a renal allograft recipient's risk for acute rejection and allograft loss.

The kits comprise primers for the 23 member gene signature set, a housekeeping gene panel for TREx and Nanostring assays (Example 6), primers for housekeeping genes for qPCR assays including beta actin (ACTB) and glyceraldehyde 3-phosphate dehydrogenase, (GAPDH), and a control probe, 18S ribosomal RNA.

A kit can further comprise one or more mRNA extraction reagents and/or reagents for cDNA synthesis. In other embodiments, the kit can comprise, one or more containers into which the biological agents are placed and, preferably, suitably aliquotted. The kit may also contain printed instructions for use of the kit materials.

The components of the kits may be packaged either in aqueous media or in lyophilized form. The kits may also comprise one or more pharmaceutically acceptable excipients, diluents, and/or carriers. Non-limiting examples of pharmaceutically acceptable excipients, diluents, and/or carriers include RNAase-free water, distilled water, buffered water, physiological saline, PBS, Ringer's solution, dextrose solution, reaction buffers, labeling buffers, washing buffers, and hybridization buffers.

The kits of the invention can take on a variety of forms. Typically, a kit will include reagents suitable for determining gene set expression levels (e.g., those disclosed herein) in a sample. Optionally, the kits may contain one or more control samples. In addition, the kits, in some cases, will include written information (indicia) providing a reference (e.g., predetermined values), wherein a comparison between the gene expression levels in the subject and the reference (predetermined values) is indicative of a clinical status.

In conclusion, a 23-gene set has been identified whose expression in whole blood at baseline is able to accurately predict early and late AR and graft loss in kidney transplant recipients, better than baseline demographic/clinical characteristics. This set, validated in two independent cohorts, was particularly accurate in predicting these events in the patients with ≤4 HLA mismatches with the donor which is the majority (60-70%) of transplant patients. Therefore, the gene-set optimally predicts the risk of acute rejection, allowing physicians the ventral folks to stratify patients at the time of transplant and tailor immunosuppression accordingly.

The present invention is described further below in Examples which are intended to further describe the invention without limiting the scope thereof.

Example 1: RNA Sequencing Assay: Identification of 23-Gene Set and its Application to Predict ACR RNA Sequencing Assay Kit Includes:
1) Illumina TruSeq mRNA Library Prep Kit
2) TruSeq RNA Single Indexes Set
3) QIAGEN RNeasy® Kit for extraction of high quality total RNA Methods for RNA Sequencing and Data Processing:

Total RNA was extracted from whole blood drawn from kidney transplant recipients prior to transplantation (baseline) using a QIAGEN RNeasy® Kit, and the libraries were generated with a TruSeq mRNA Library Prep Kit and were further multiplexed with TruSeq RNA Single Indexes. The indexed libraries were sequenced on an Illumina HiSeq4000 sequencer. The reads with good quality were first aligned to human reference databases including the hg19 human genome, exon, splicing junction segment and contamination database including ribosomal and mitochondrial sequences using the well-known BWA alignment algorithm. After filtering for reads that 3 mapped to the contamination database, the reads that are uniquely aligned to the exon and splicing-junction segments with a maximum of 2 mismatches for each transcript were then counted as the expression level for each corresponding transcript. The read counts were log 2 transformed and normalized at an equal global median value in order to compare transcription levels across samples.

Results

Patient cohort description: This study included a total of 235 patients with good quality baseline blood RNAs that underwent RNA sequencing. Out of them, 155 had available information on surveillance biopsies taken serially before and after transplant, while 80 only had information on surveillance biopsies taken between months 6 to 24 after transplant. Out of 155 patients with early surveillance biopsies, 81 were randomly selected to be used as the discovery set for the identification of the gene signature set for predicting early acute rejection (EAR). Patients were diagnosed based on their inflammation or tubulitis score (1 or above) from kidney biopsies obtained before 6 month after transplant. The discovery set with well-characterized EAR and non-EAR diagnoses was used to identify the gene set and derive the p values and the median expression values of the EAR and the non-EAR groups for the calculation of the risk score. The remaining 74 patients were used as the first validation cohort (V1). The 80 patients with later surveillance biopsies were used as the second validation cohort (V2).

(b) Identification of the 23 gene set: RNA sequencing was performed on the discovery set of 81 patients. After a series of read quality controls, mapping and normalization steps were performed on the raw sequence reads (4). The normalized read counts obtained were used as the expression values of the genes. The expression values for the EAR and the non-EAR groups in the discovery set (N=81) were compared by the well-known LIMMA (5) test. 688 upregulated and 653 downregulated differentially expressed genes (DEGs) were identified. Using the risk score based on the comparison of gene expression to the median value of the EAR or the No-EAR groups, a 23 gene set with the best predictive value was identified from the DEGs with 100 iteration steps in the discovery set (N=81, AUC=0.80). The formula employed for the risk score, r is described above.

(c) To estimate the prediction accuracy: two tertile cutoffs for the gene risk scores (32 or −23) were defined and demonstrated positive predictive value (PPV)>0.70 and negative predictive value (NPV)>0.88 for prediction of EAR in the discovery set.

(d) Application of the 23 gene set on two validation sets for early and late acute rejection or graft loss prediction: The prediction of early acute rejection by the 23-gene set was validated using a V1 dataset (N=74, AUC=0.74, PPV=0.70, NPV=0.88), at the tertile cutoffs (32 and −23) defined from the discovery set) performed better in allograft recipients with less than 4 HLA mismatches (AUC=0.89, PPV=0.75 and NPV=1). The risk score derived from the gene set was also significantly associated with AR after 6 months post-transplant and long-term graft loss in the two validation sets (N=154 (V1+V2), P=0.041 for acute rejection and P=0.034 for graft loss), especially in recipients of allografts with ≤4 HLA mismatches (P=0.005 for AR and P=1.57e-4 for graft loss).

Overall, the risk score accurately predicted graft loss at any time (AUC=0.804~0.904) and the prediction reached an AUC>0.80 with patients with ≤4 HLA mismatches. When only graft loss within 2 years after transplant were considered, the AUC for patients with ≤4 HLA mismatches was 0.904, while AUC for graft loss before 5 years was 0.820.

Example 2: Use of the Cumulative Risk Score Formula to Calculate the Risk Score for a Given Patient 1) Calculate the p value and the median value of the EAR and the non-EAR group for each gene from the discovery set or the training set (see Column "EAR_Med", "non-EAR_Med" and "P Value" in the attached table):

2) For a patient with expression data for the 23 gene (Column "Patient"), calculate the logic number g (column "g")

3) Calculate log 10(p)*g for each gene (Column "−log 10(p)*g)

4) Add up log 10 (p)*g for the 23 genes to get a risk score of 65.94 which is higher than the 32 cutoff

| Symbol | EAR_Med | Non-EAR_Med | P Value | Direction | Patient | g | -log10 (p) | -log10 (p)*g |
|---|---|---|---|---|---|---|---|---|
| F12 | 8.61 | 8.03 | 1.58E-03 | Up | 8.26 | 0 | 2.80 | 0.00 |
| SLC25A34 | 7.04 | 6.54 | 1.46E-04 | Up | 7.53 | 1 | 3.83 | 3.83 |
| PRKCH | 11.02 | 11.41 | 2.78E-03 | Down | 10.19 | 1 | 2.56 | 2.56 |
| HOPX | 8.61 | 9.05 | 1.55E-03 | Down | 7.35 | 1 | 2.81 | 2.81 |
| CCDC102A | 7.94 | 8.48 | 2.60E-03 | Down | 6.70 | 1 | 2.59 | 2.59 |
| LDOC1L | 8.48 | 9.04 | 5.33E-04 | Down | 8.11 | 1 | 3.27 | 3.27 |
| CCR5 | 8.91 | 9.49 | 4.23E-03 | Down | 7.33 | 1 | 2.37 | 2.37 |
| C1orf21 | 8.15 | 8.74 | 9.98E-05 | Down | 6.55 | 1 | 4.00 | 4.00 |
| ZNF831 | 8.86 | 9.46 | 7.68E-04 | Down | 7.89 | 1 | 3.11 | 3.11 |
| CD8A | 11.50 | 12.11 | 3.69E-03 | Down | 11.01 | 1 | 2.43 | 2.43 |
| TOX | 7.03 | 7.71 | 1.57E-04 | Down | 6.26 | 1 | 3.80 | 3.80 |
| TBX21 | 10.98 | 11.67 | 2.09E-03 | Down | 9.63 | 1 | 2.68 | 2.68 |
| FASLG | 6.72 | 7.46 | 2.45E-04 | Down | 4.91 | 1 | 3.61 | 3.61 |
| FCRL6 | 8.60 | 9.34 | 1.58E-03 | Down | 7.80 | 1 | 2.80 | 2.80 |
| TARP | 10.45 | 11.20 | 2.41E-03 | Down | 9.17 | 1 | 2.62 | 2.62 |
| LAG3 | 8.19 | 9.00 | 2.00E-03 | Down | 7.59 | 1 | 2.70 | 2.70 |
| KIAA1671 | 6.87 | 7.68 | 2.50E-04 | Down | 6.11 | 1 | 3.60 | 3.60 |

-continued

| Symbol | EAR_Med | Non-EAR_Med | P Value | Direction | Patient | g | -log10 (p) | -log10 (p)*g |
|---|---|---|---|---|---|---|---|---|
| PRF1 | 12.76 | 13.61 | 2.22E−03 | Down | 11.15 | 1 | 2.65 | 2.65 |
| NKG7 | 13.70 | 14.57 | 1.31E−03 | Down | 11.83 | 1 | 2.88 | 2.88 |
| FGFBP2 | 10.78 | 11.73 | 1.39E−03 | Down | 9.51 | 1 | 2.86 | 2.86 |
| S1PR5 | 10.17 | 11.18 | 9.10E−04 | Down | 8.83 | 1 | 3.04 | 3.04 |
| ADGRG1 | 10.90 | 12.02 | 9.52E−04 | Down | 9.67 | 1 | 3.02 | 3.02 |
| GZMH | 10.55 | 11.90 | 2.05E−03 | Down | 9.51 | 1 | 2.69 | 2.69 |
| | | | Risk Score: | | | | | 65.94 |

Example 3: Targeted RNA Expression (TREx) Assay

1) Custom Assay kit (primer sets for the 23 gene panel and a housekeeping gene panel (Example 6) and reagents)
2) Illumina® TruSeq® RNA Sample Preparation Kit v2
3) TruSeq RNA Single Indexes Set
4) QIAGEN RNeasy® Kit for extraction of high quality total RNA Targeted Expression TREx Experiments:

The total RNA will be extracted using the QIAGEN RNeasy® Kit. The sequencing library will be generated using the Illumina® TruSeq® RNA Sample Preparation Kit v2 by following the manufacturer's protocol: briefly, polyA-containing mRNA will be first purified and fragmented from the total RNA. The first-strand cDNA synthesis will be performed using random hexamer primers and reverse transcriptase followed by the second strand cDNA synthesis. After the endrepair process, which converts the overhangs into blunt ends of cDNAs, multiple indexing adapters will be added to the end of the double stranded cDNA. PCR will be performed to enrich the targets using the primer pairs specific for the gene panel and housekeeping genes. Finally, the indexed libraries will be validated, normalized and pooled for sequencing on the MiSEQ sequencer.

TREx Data Processing:

The raw RNAseq data generated by the MiSEQ sequencer will be processed using the following procedure: The reads with good quality will be first aligned to several human reference databases including the hg19 human genome, exon, splicing junction and contamination databases, including ribosomal and mitochondrial RNA sequences, using the BWA1 alignment algorithm. After filtering reads that mapped to the contamination database, the reads that are uniquely aligned with a maximum of 2 mis-matches to the desired amplicon (i.e. PCR product from the paired primers) regions will be then counted as the expression level for the corresponding gene and further subjected to normalization based on the expression of the housekeeping genes.

Example 4: Nanostring Assay

1) Custom CodeSet (barcoded probesets for the 23 gene panel, housekeeping gene panel (Example 6) and negative controls provided by Nanostring).
2) nCounter® Master Kit including nCounter Cartridge, nCounter Plate Pack and nCounter Prep Pack.
3) QIAGEN RNeasy® Kit for extraction of high quality total RNA Nanostring Experiments:

Total RNA will be extracted using the QIAGEN RNeasy® Kit by following the manufacturer's protocol; Barcode probes will be annealed to the total RNA in solution at 65° C. with the master kit. The capture probe will capture the target to be immobilized for data collection. After hybridization, the sample will be transferred to the nCounter Pre Station and the probe/target will be immobilized on the nCounter Cartridge. The probes are then counted by the nCounter Digital Analyzer.

mRNA Transcriptomic Data Analysis

The raw count data from the Nanostring analyzer will be processed using the following procedure: the raw count data will be first normalized to the count of the housekeeping genes and the mRNAs with counts lower than the median plus 3 standard deviation of the counts of the negative controls will be filtered out. Due to data variation arising from the use of different reagent lots, the count for each mRNA from each different reagent lot will be calibrated by multiplying a factor of the ratio of the averaged counts of the samples on different reagent lots. The calibrated counts from different experimental batches will be further adjusted using the ComBat package.

Example 5: qPCR Assay

1) Primer container (26 tubes with one qPCR assay per tube for each of the 23 genes, which include the 23 gene-panel and 2 housekeeping genes (ACTB and GAPDH) and the control probe (18S ribosomal RNA). The assays are obtained from LifeTech.
2) TaqMan® Universal Master Mix II: reagents for qPCR reactions
3) TaqMan® ARRAY 96-WELL PLATE (6×23).
4) Agilent AffinityScript QPCR cDNA Synthesis Kit: for the highest efficiency of converting RNA to cDNA and fully optimized for real-time quantitative PCR (QPCR) applications.

Total RNA will be extracted from the allograft biopsy samples using the ALLprep kit (QIAGEN-ALLprep kit, Valencia, Calif. USA). cDNA will be synthesized using the AffinityScript RT kit with oligo dT primers (Agilent Inc. Santa Clara, Calif.). TaqMan qPCR assays for the 23-gene signature set, 2 housekeeping genes (ACTB, GAPDH) and 18S ribosomal RNA will be purchased from ABI Life Technology (Grand Island, N.Y.). qPCR experiments will be performed on cDNAs using the TAQMAN universal mix and PCR reactions will be monitored and acquired using an ABI7900HT system. Samples will be measured in triplicate. Cycle Times (CT) values for the prediction gene set as well as the 2 housekeeping genes will be generated. The ACT value of each gene will be computed by subtracting the average CT value for the housekeeping genes from the CT value of each gene.

Example 6: Housekeeping Gene Panel for Use in the Present Invention

Presented below are 13 housekeeping gene candidates that can be used as gene panels to monitor the quality in the assays of the present invention. 10 genes per panel are used to monitor the quality of the reactions. The kits also contain primers for the housekeeping genes. The 10 housekeeping genes are selected from the group consisting of CHTOP, YKT6, RER1, PI4KB, ZDHHC5, TMEM248, C6orf89, SMU1, SHC1, DLST, UBE2Q1, FBXO18 and SLC35E1.

REFERENCES

Mengel, M. et al. Banff 2011 Meeting report: new concepts in antibody-mediated rejection. *Am J Transplant* 12, 563-70 (2012).
2. Yilmaz, S. et al. Protocol core needle biopsy and histologic Chronic Allograft Damage Index (CADI) as surrogate end point for long-term graft survival in multicenter studies. *J Am Soc Nephrol* 14, 773-9 (2003).
3. Solez, K. et al. Banff 07 classification of renal allograft pathology: updates and future directions. *Am J Transplant* 8, 753-60 (2008).
4. Li H. and Durbin R. (2009) Fast and accurate short read alignment with Burrows-Wheeler Transform. Bioinformatics, 25:1754-60 [PMID: 19451168]
5. Ritchie M E, Phipson B, Wu D, Hu Y, Law C W, Shi W and Smyth G K (2015). "limma powers differential expression analyses for RNA-sequencing and microarray studies." *Nucleic Acids Research,* 43(7), pp. e47.

A number of embodiments of the invention have been described. Nevertheless, it will be understood that various modifications may be made without departing from the spirit and scope of the invention. Accordingly, other embodiments are within the scope of the following claims.

It is further to be understood that all values are approximate, and are provided for description. Patents, patent applications, publications, product descriptions, and protocols are cited throughout this application, the disclosures of which are incorporated herein by reference in their entireties for all purposes.

What is claimed is:
1. A method of identifying and treating a renal allograft candidate at risk of developing acute rejection comprising the steps of
   (a) determining the RNA expression levels of each of the genes in a gene signature set in a pre-transplant blood specimen from the renal allograft candidate, said gene signature set including GZMH, ADGRG1, S1PR5, FGFBP2, NKG7, PRF1, KIAA1671, LAG3, TARP, FCRL6, FASLG, TBX21, TOX, ZNF831, CD8A, C1orf21, CCR5, LDOC1L, CCDC102A, HOPX, PRKCH, SLC25A34 and F12;
   (b) comparing the RNA expression levels of each of the genes in the gene signature set with the RNA expression levels of each of the genes of a gene signature set in a control sample obtained from a renal allograft recipient that did not suffer acute renal rejection, and calculating a cumulative risk score based on the differences in RNA expression between the genes of the gene signature sets,
   (c) identifying the renal allograft candidate as being at risk for allograft rejection based on the calculated cumulative risk score, and
   (d) treating the renal allograft candidate identified in (c) as being at risk of acute allograft rejection by administering an induction therapy to the allograft candidate.
2. The method of claim 1 wherein the difference in RNA expression level comprises an increase or a decrease in the RNA expression level of one or more genes in the gene signature set in the specimen compared to the same one or more genes in the gene signature set in the control.
3. The method of claim 2 wherein the RNA expression levels are determined by a method selected from the group consisting of Nanostring analysis, TREx analysis and quantitative polymerase chain reaction (qPCR) analysis.
4. A method of identifying and treating a candidate for a renal allograft transplant at risk of acute rejection of the allograft before transplantation comprising the steps of
   (a) obtaining a blood specimen from the renal allograft candidate;
   (b) isolating mRNA from the blood specimen;
   (c) synthesizing cDNA from the mRNA;
   (d) determining the RNA expression levels of each of the genes of a gene signature set in said renal allograft candidate's blood from the cDNA obtained in (c), said gene signature set including GZMH, ADGRG1, S1PR5, FGFBP2, NKG7, PRF1, KIAA1671, LAG3, TARP, FCRL6, FASLG, TBX21, TOX, ZNF831, CD8A, C1orf21, CCR5, LDOC1L, CCDC102A, HOPX, PRKCH, SLC25A34 and F12;
   (e) identifying the renal allograft candidate as being at risk for acute rejection by comparing the RNA expression levels of each of the genes in the gene signature set in the renal allograft candidate's blood specimen with the expression levels of each of the genes in a control blood specimen obtained from a renal allograft recipient that did not suffer acute renal rejection and calculating a cumulative risk score based on the differences in RNA expression between the genes of the gene signature sets, and
   (f) administering an induction therapy to the renal allograft candidate identified in (e) as being at risk for acute rejection.
5. The method of claim 4 wherein said induction therapy comprises administering a therapeutically effective amount of anti-thymocyte globulin or Campath-1H.
6. The method of claim 4 wherein the RNA expression levels are determined by a method selected from the group consisting of Nanostring, TREx, and quantitative polymerase chain reaction (qPCR).
7. A method of selecting a renal allograft candidate for induction therapy and administering the induction therapy to the selected renal allograft candidate before transplantation to reduce the risk of acute renal rejection which comprises
   (a) comparing the RNA expression levels of each of the genes of a gene signature set obtained from the renal allograft candidate with the RNA expression levels of each of the genes of a gene signature set in a control sample obtained from a renal allograft recipient that did not suffer acute renal rejection and calculating a cumulative risk score based on the differences in RNA expression between the genes of the gene signature sets;
   (b) selecting the renal allograft candidate for treatment with induction therapy based on the cumulative risk score, said gene signature set including GZMH, ADGRG1, S1PR5, FGFBP2, NKG7, PRF1, KIAA1671, LAG3, TARP, FCRL6, FASLG, TBX21, TOX, ZNF831, CD8A, C1orf21, CCR5, LDOC1L, CCDC102A, HOPX, PRKCH, SLC25A34 and F12; and
   (c) administering an induction therapy to the renal allograft candidate selected in (b).

8. The method of claim 7 wherein said induction therapy comprises administering a therapeutically effective amount of anti-thymocyte globulin or Campath-1H.

* * * * *